United States Patent [19]

Hetz

[11] Patent Number: 4,869,258

[45] Date of Patent: Sep. 26, 1989

[54] INTRACAVITARY ULTRASOUND SCANNER MEANS

[75] Inventor: Walter Hetz, Erlangen, Fed. Rep. of Germany

[73] Assignee: Siemens Aktiengesellschaft, Berlin and Munich, Fed. Rep. of Germany

[21] Appl. No.: 128,441

[22] Filed: Dec. 3, 1987

[30] Foreign Application Priority Data

Dec. 5, 1986 [DE] Fed. Rep. of Germany ....... 3641280

[51] Int. Cl.$^4$ .............................................. A61B 8/12
[52] U.S. Cl. ........................... 128/660.10; 128/662.06
[58] Field of Search ....................... 128/660.09, 660.10, 128/662.05, 662.06, 4, 6

[56] References Cited

U.S. PATENT DOCUMENTS

| 3,600,613 | 8/1971 | Clarke | 128/660 |
| 4,034,744 | 7/1977 | Goldberg | 128/660 |
| 4,181,120 | 1/1980 | Kunii et al. | 128/660 |
| 4,426,886 | 1/1984 | Finsterwald et al. | 128/660 |

FOREIGN PATENT DOCUMENTS

| 0139574 | 1/1984 | European Pat. Off. | 128/660 |
| 2636107 | 2/1978 | Fed. Rep. of Germany | 128/660 |
| 3618082A1 | 12/1986 | Fed. Rep. of Germany | 128/660 |
| 1578405 | 11/1980 | United Kingdom | 128/660 |

Primary Examiner—Francis Jaworski
Attorney, Agent, or Firm—Hill, Van Santen, Steadman & Simpson

[57] ABSTRACT

A first ultrasound transducer (24) is mounted in the interior of an examination head (4), which is rotatable around an axis (26) by means of first and second gears (52, 56) and by means of a drive shaft (22) which is driven by an electric motor (106) for scanning a first examination surface. The axis (26) is aligned perpendicular to the distal end of the drive shaft (22). The two gears (52, 56) are preferably fashioned as bevel gears. The second gear (56) is secured to the end of the drive shaft (22) and has a depression (60) into which the first ultrasound transducer (24) passes when it turns. A compact structure is achieved in this way. A second ultrasound transducer (90) is secured to the second bevel gear (56), which turns around the drive shaft (22) and thereby scans a second examination surface having the shape of an envelope of a cone which is positioned not entirely perpendicular relative to the first examination plane. Both transducers (24, 90) are rotatorily driven by the same drive shaft (22), which results in a simple design. The device is particularly suitable for vaginal and rectal examinations.

36 Claims, 5 Drawing Sheets

INTRACAVITARY ULTRASOUND SCANNER MEANS

BACKGROUND OF THE INVENTION

1. Field of the Invention

The invention is directed to an intracavitary ultrasound scanner means comprising an examination head with an interior which contains an ultrasound transducer and the ultrasound transducer is rotatable around an axis and is driven with a drive shaft.

2. Description of the Prior Art

Ultrasound scanning means of the said species described in (Ultrasound in Med. and Biol., Vol. 5, Pages 129-138, "A High-Resolution Transrectal Ultrasonography System") and are commercially available. They usually contain a single, mechanically moved ultrasound transducer which is either oscillated back and forth or rotated. Body cavities such as, for example, the rectum or the vagina, are examined with such scanner means. It is desired that the examination head be built as small as possible given high performance capability.

According to FIGS. 2 and 3 of German Published application 36 18 082, an ultrasound transducer at the end of the measuring head arrangement is mounted in a rotational fashion on a shaft in an ultrasound measuring head arrangement for medical diagnostics, the shaft extending perpendicularly to a drive shaft. The drive of the transducer occurs with a bevel gear. However, a second ultrasound transducer with which observation in a second plane of section is possible is not provided therein. Further, the measuring head arrangement shown therein is not suitable for intracavitary examinations because of its large outside dimensions.

European Patent publication 0,139,574 also discloses an intracavitary ultrasound scanner means wherein work is carried out with two ultrasound transducer arrangements. The examination surfaces or planes of sections in the known apparatus are perpendicular to one another. In the known apparatus, the one ultrasound transducer is mechanically moved whereas electronic scanning is carried out with the other ultrasound transducer which is a linear array. Observation of sections on two planes perpendicular to one another enables the observer to carry out a more precise diagnosis than an examination in only a single scanning plane. Size and position of interesting objects can be more easily identified in this fashion.

As has already been mentioned an examination head of the said species should comprise an optimally small structural size.

SUMMARY OF THE INVENTION

It is an object of the present invention to provide an ultrasound scanner means of the species initially cited wherein the examination head is fashioned such that a precise observation and examination of the region of interest is possible in two scanning planes without modifying the position of the ultrasound scanner means. The examination head should comprise a compact structure. As viewed in longitudinal direction of its drive shaft, it should thus be relatively short. Its one scanning plane should lie in the longitudinal direction (or offset parallel thereto) and the other should lie obliquely or roughly perpendicularly relative thereto.

This object is inventively achieved in that the shaft is aligned essentially perpendicular to the distal end of the drive shaft and a first gear is provided for turning the ultrasound transducer around the shaft, this first gear meshes with a second gear secured at the distal end of the drive shaft; and in a holding part which is connected to the drive shaft is provided, a further ultrasound transducer is secured to this holding part.

The emission direction of the further ultrasound transducer can thereby be aligned in a slant direction relative to the radial plane of the drive shaft. A mechanical ultrasound scanner for body cavities is obtained in this manner which has the possibility of scanning two examination surfaces which lie either perpendicularly relative to one another or, as mentioned, nearly perpendicularly relatively to one another. Also, achieved in this design is that the pivot points of the sectors that are seen on the two picture screens lie rather close to one another. At the same time, only a single drive, namely, the drive shaft, is required for both ultrasound transducers.

Two gears mounted essentially perpendicularly relative to one another are employed and, a compact structure of the examination head is achieved. What is thereby meant by the term "axis" is a three-dimensionally fixed orientation line. In a practical realization, for example, this involves a rotatable shaft or a bearing shaft which is arranged so that it is fixed three-dimensionally.

Fundamentally, helical gears can be used. In a preferred development, however, the first and second gears are a first or, respectively, second bevel gear and the bevel gear has a distally placed depression into which the ultrasound transducer dips when turning around the axis. Space in the longitudinal direction is thus saved by using the said depression.

A further advantageous development is characterized in that the first ultrasound transducer is rigidly coupled to the drive shaft and in that the second ultrasound transducer is coupled to the drive shaft via a releasable coupling. In a further development, the second ultrasound transducer is provided for producing a B-image when it is coupled to the drive shaft and is provided for the implementation of a Doppler flow measurement when it is uncoupled from the drive shaft. It is advantageous that the alignment of the examination head relative to the specimen to be examined can be precisely observed in two examination planes. During the Doppler flow measurement following, a positional change of the examination head or of the specimen in the body can be immediately recognized via the sector scanning of the first ultrasound transducer at the same time and can be corrected.

Another advantageous embodiment of the intracavitary ultrasound scanner means is that a biopsy needle guide which encompasses a guide tube and a clamp mechanism is detachably connected to the examination head, and when the guide tube is arranged so that is laterally offset and extends in the direction of the drive shaft, and the discharge opening of the guide tube can be aligned in a slanting direction relative to the drive shaft. The combination of the ultrasound scanner means with the biopsy needle guide is especially advantageous because the biopsy needle used for the implementation of the biopsy can be observed via the two examination surfaces which are perpendicular or nearly perpendicular relative to one another. Impediments in the feed path of the biopsy needle which are not visible in the one examination surface can thus be recognized in the other examination surface. The alignment of the discharge opening of the guide tube at a slant relative to the drive shaft allows tissue or fluid specimens to be taken from the inside of the body via the wall of the body cavity.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

DESCRIPTION OF THE PREFERRED EMBODIMENTS

Figure 1:
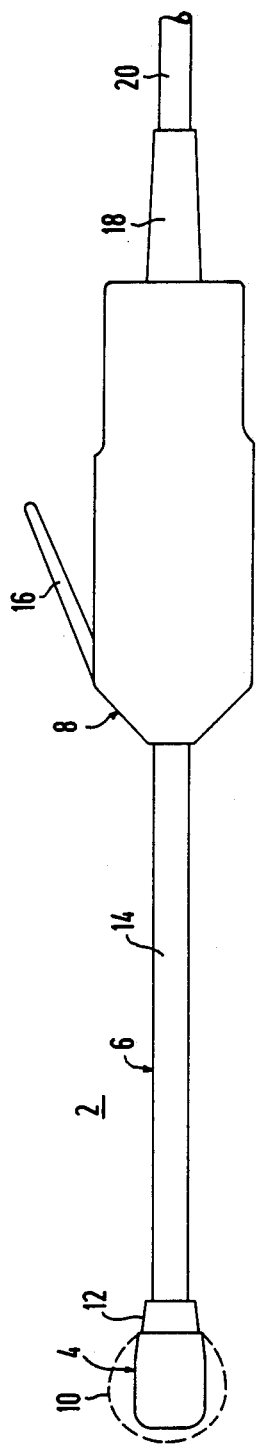
FIG. 1 is a side view of an intracavitary ultrasound scanner means of the invention.

FIG. 1 illustrates the essential component parts mounted in an ultrasound scanner means 2 for body cavities and includes an examination head 4, a straight-line guide 6 and an endpiece or a housing head 8. The ultrasound scanner means 2—as set forth in greater detail below—is fashioned such that, after introduction of the examination head 4 into the body cavity, an examination can be carried out on two examination surfaces which lie essentially perpendicularly relative to one another without the scanner means 2, when observing an object having to be moved in the longitudinal direction of the guide 6 upon switching from the first examination surface in the second examination surface. The two examination surfaces can be portrayed successively or simultaneously on one or two picture screens, for example, as conventional sector images. The examination head 4 is formed especially short in the longitudinal direction. The result is that the pivot points of the two sectors portrayed on the picture screen or picture screens lie extremely close to one another.

It may be seen from FIG. 1 that the examination head 4 is surrounded by a cladding 10 of an elastic material, for example, rubber. This cladding 10 can be inflated in a known way in order to achieve good contact against the cavity wall and, thus, good ultrasound coupling. The inflated condition of the cladding 10 is shown in broken lines. The cladding 10 is attached to the examination head 4 with a tightening nut 12. The guide 6 is formed to be rigid and connects the examination head 4 to the housing head 8. It is provided with a plastic cladding 14 on the outside.

In a known way, the housing head 8 contains an electric motor having a position generator and serves as the manipulator during the examination. In the present case, it also contains a pump (not shown) for inflating the cladding 10 via the guide 6. Only the pump actuation lever 16 of this pump is shown. Alternatively, this lever 16 can also be a lever for actuating a valve for the purpose of inflating the cladding 10 or for the purpose of releasing the pressure therein. Electrical connecting lines lead from the housing head 8 through the guide 6 to the examination head 4; and further connecting lines are provided for conducting signals from the examination head 4 through the guide 6 to the housing head 8. After passing through an anti-kink socket 18, all of these lines in the form of an electrical connecting cable 20 are connected to a known ultrasound B-image apparatus. In a traditional way, this serves the purpose for generating transmission pulses, signal evaluation and image portrayal. The B-imaging apparatus can be switched between the two ultrasound tomograms listed below. Instead, two tomograms can also be portrayed in real time.

Figure 2:
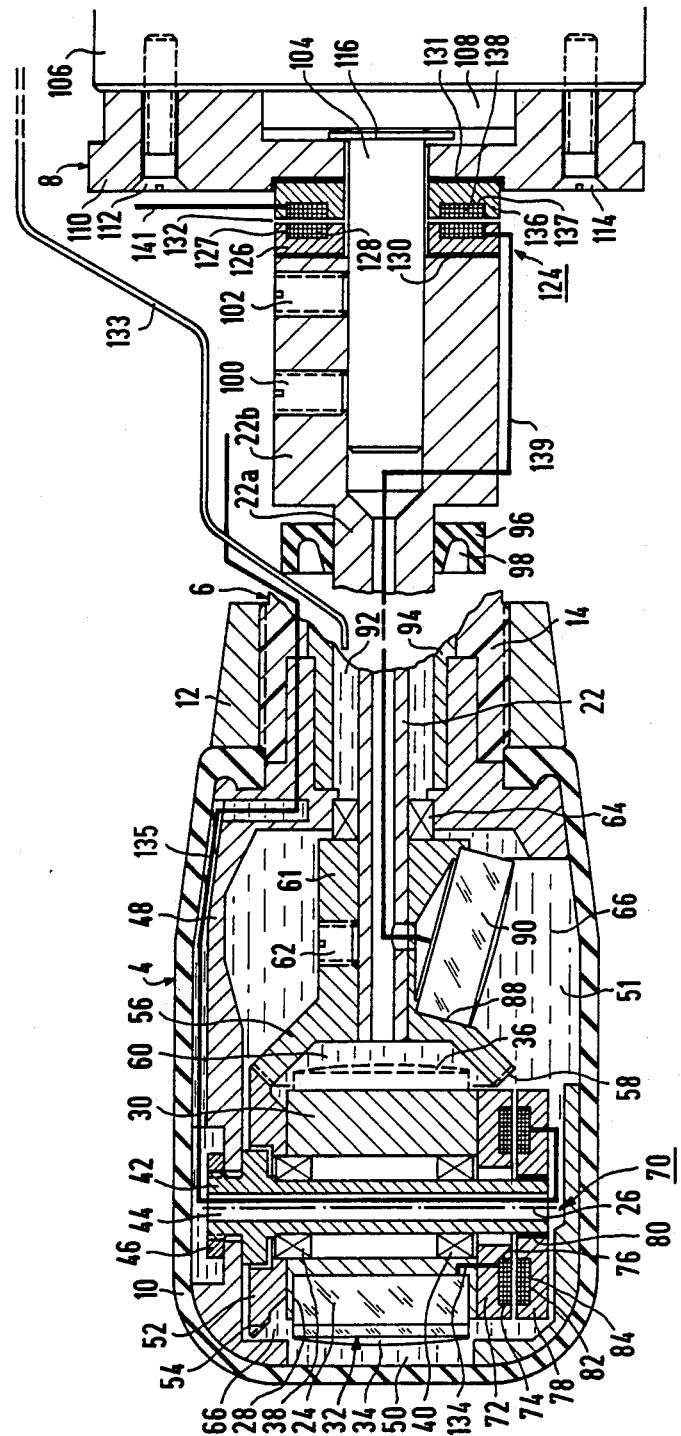
FIG. 2 is a sectional view through the ultrasound scanner of FIG. 1.

FIG. 2 illustrates the details of the examination head 4, the guide 6 and the housing head 8 in section. The cladding of the housing head 8 is not shown.

In the specification, "distal" means far from the origin and the distal end of a drive shaft is the end located remotely from the source of the driving energy. "Proximal" means near the origin of the power source.

As shown in FIG. 2, a drive shaft 22 extends from the housing head 8 to the examination head 4 and serves the purpose of turning a first ultrasound transducer 24 around an axis 26. The axis 26 is aligned perpendicular to the distal end section of the drive shaft 22. The drive shaft 22 is formed as a hollow shaft. It lies centrally in the guide 6 and is preferably composed of a metal.

The first ultrasound transducer 24 is cylindrically formed. It is seated in a substance 28 which is accommodated in a cylindrical body or in a drum 30. This drum 30 can turn around the axis 26. The emission surface 32 of the first ultrasound transducer 24 has a lens 34. This, for example, can be composed of silicon rubber. Instead of a single ultrasound transducer 24, a plurality of such transducers can also be arranged which are offset at the circumference of the drum 30. In the illustrated position, the emission surface 32 of the ultrasound transducer 24 is directed toward the left. When turned around the axis 26, an examination plane is thus scanned, this examination plane being perpendicular relative to the plane of the paper and, in the illustrated exemplary embodiment, specifically coinciding with the longitudinal axis of the drive shaft 22. The position of the emission surface 32 which is rotated by 180° is shown in broken lines and is referenced 36. It corresponds to the maximum immersed position of the first ultrasound transducer 24 into the interior of the examination head 4 when turning around the axis 26.

The drum 30 serves as a sonic head carrier and is seated on a bearing shaft 42 with two ball bearings 38, 40. This bearing shaft 42 is formed as a hollow shaft in order to enable electrical lines to be conducted therethrough. Its axis of symmetry is the axis 26 which extends centrally through the channel 44. The bearing shaft 42 is arranged three-dimensionally rigid in the inside of the examination head 4. To that end, it is screwed to a housing 48 at one end, for example, with a nut 46. This housing 48 can, in particular, be composed of plastic, but is preferably composed of metal. It has a first ultrasound window 50 which is arranged at the distal face wall and which is provided for the first ultrasound transducer 24 and also has a second ultrasound window 51 (not shown) which lies in the radial direction. The housing 48 is secured to a carrying tube 94.

A first bevel gear 52 is secured to the one face end of the drum 30 close to the housing wall. Drum 30 and gear wheel 52 thus turn in common around the axis 26. The first gear wheel 52 is, in particular, fashioned as a bevel gear. The teeth 54 lie at an angle of 45° relative to the axis 26. This first gear 52 has teeth 54 which mesh with a second gear 56 which is secured to the distal end of the drive shaft 22. This second gear wheel 56 is likewise fashioned as a bevel gear. It has a recess or depression 60 between its teeth 58 and the first ultrasound transducer 24 can be turned through this recess or depression 60. As a result of the depression 60, a relatively small structural size in the longitudinal direction of the drive shaft 22 can be achieved. At its proximal end, the second gear 56 has a holding part 61 which is secured to the drive shaft 22 with a set screw 62. One of the two gears 52 and 56 which mesh with one another is particularly composed of a metal and the other is composed of a plastic in order to keep the development of noise low. The second gear 56 lies inside the housing 48. A further ball bearing 64 which is secured to the housing 48 is situated at its end and this further ball bearing 64 centrally guides the drive shaft 22 in its end region. All ball bearings 38, 40 and 64 are permeable to a coupling fluid 66 which serves the purpose of a good ultrasound transmission and with which the interior of the examination head 4 and of the guide 6 are filled.

It is necessary to supply the first ultrasound transducer 24 with electrical pulses and to take electrical signals therefrom. A variable transformer 70 is provided for this purpose. This variable transformer 70 is composed of a rotating and of a non-rotating part. The rotating part surrounds an annular carrying part 72 which is secured to the second end face of the drum 30. A transformer coil 76 lies in an annular groove 74. The stationary part of the variable transformer 70 is mounted so that is separated therefrom by a slight air gap. This stationary part of the variable transformer 70 comprises an annular carrying part 78 which is secured to the end of the stationary bearing shaft 42 with an adhesive 80. It contains an annular groove 82 in which a further coil 84 is accommodated. A non-galvanic signal transmission is possible with the assistance of the variable transformer 70.

A substance 88 is provided in the holding part 61 of the second gear 56. A second, cylindrical ultrasound transducer 90 is situated in the substance 88. It is noteworthy that the second ultrasound transducer 90 is accommodated in the proximity of the first ultrasound transducer 24. The origins of the two, central emission axes thus lie relatively close to one another. It should also be emphasized that this second ultrasound transducer 90 is aligned somewhat obliquely relative to the drive shaft 22. This results therein that the ultrasound beam repeatedly emitted by this ultrasound transducer 90 describes the envelope of a cone when the drive shaft 22 turns, this conical envelope lying centrally with respect to the drive shaft 22. The oblique position of the second ultrasound transducer 90 is selected in order to acquire the object of interest in the images produced by the ultrasound transducer 24, 90 without having to alter the position of the examination head 4 with respect to the object. Since the scan surface of the second ultrasound transducer 90 intersects the scan plane of the first ultrasound transducer 24 at a slant, an object can be equally well-observed in the appertaining picture screen images (central position).

Next, the guide 6 shall be considered again. It encompasses the drive shaft 22 guided in the ballbearing 64 for turning both ultrasound transducers 24, 90. In the region of the housing head, this drive shaft is enlarged step-shaped and is increased in wall thickness. The strengthened drive section is referenced 22a. An inter space 92 is free, and the drive shaft 22 is surrounded by a stationary carrying tube 94. This, in particular can be composed of metal. The flexible cladding 14 is slipped onto the carrying tube 94. A sealing ring 96 which is provided with an annular groove 98 at the side of the examination head 4 is mounted on the strengthened drive shaft section 22a. The coupling fluid 66 extends up to this annular groove 98.

An end section 22b of the drive shaft 22 follows the section 22a. This has its wall thickness further reinforced. The inside diameter is also increased. The section 22b is secured to the shaft 104 of an electric motor 106 with two set screws 100, 102. The servo motor 106 is located in the housing head 8. A flange 110 is secured to its collar 108 with two counter sunk screws 112, 114. An inserted snap ring is referenced 116.

A second variable transformer 124 is mounted on the shaft 104. This second variable transformer 124 is provided for the signal communication from and to the second ultrasound transducer 90. The rotatable part of the variable transformer 124 is formed of a carrying ring 126 into whose face-end annular groove 127 a first transformer coil 128 is inserted. For example, the carrying ring 126 can be glued with an adhesive 130 to the end face of the end section 22b. The non-rotatable part of the second variable transformer 124 is located a short distance therefrom as shown by the gap 132. This second part correspondingly encompasses a carrying ring 136 in whose annular groove 137 a coil 138 is inserted. The carrying ring 136 has its end face secured to the flange 110 with an adhesive 131. It is also indicated in FIG. 2 that a hydraulic line 133 is arranged inside the housing head 8. This leads from the said manual pump of which the pump actuating lever 16 is shown in FIG. 1 to the inter space 92. Coupling fluid 66 is pumped into the interspace 92 and, thus, into the housing 48 with the assistance of this pump via the hydraulic line 133. The pressure elevation results therein so that the cladding 10 which is clamped to the housing 48 with the tightening nut 12 inflates and conforms to the wall of the examined body cavity during an ultrasound examination. Good ultrasound transmission is possible in the region of the two ultrasound windows 50, 51 in this way.

FIG. 2 also schematically shows the electrical line path for signals to and from the first or, respectively, second ultrasound transducer 24 or, respectively, 90. The lines 134, 135 or, respectively, 139, 141 are each illustrated by thicker lines. It may be seen that the electrical lines 152 extend both through the channel 44 in the bearing shaft 42 as well as in the space between housing 48 and cladding 10. They further proceed radially through the housing wall and finally proceed through the plastic cladding 14. The lines 139 between the second ultrasound transducer 90 and the second variable transformer 124 proceed through the longitudinal bore of the drive shaft 22 and then proceed on the outside cladding of the thickened end member 22b. The lines 135, 141, finally, proceed into the interior of the housing head 8.

The advantage of the intracavitary ultrasound scanner means 2 shown in FIGS. 1 and 2 is seen particularly in its simple structure and in its space-saving, compact design. Also, of significance is that only one motor-driven drive shaft 22 is provided for the mechanical movement of the two ultrasound transducers 24 and 90 which scan the different examination surfaces. In order to suppress malfunctions during operation, one must see to it that the two ultrasound transducers 24, 90 are alternately switched on.

Figure 3:
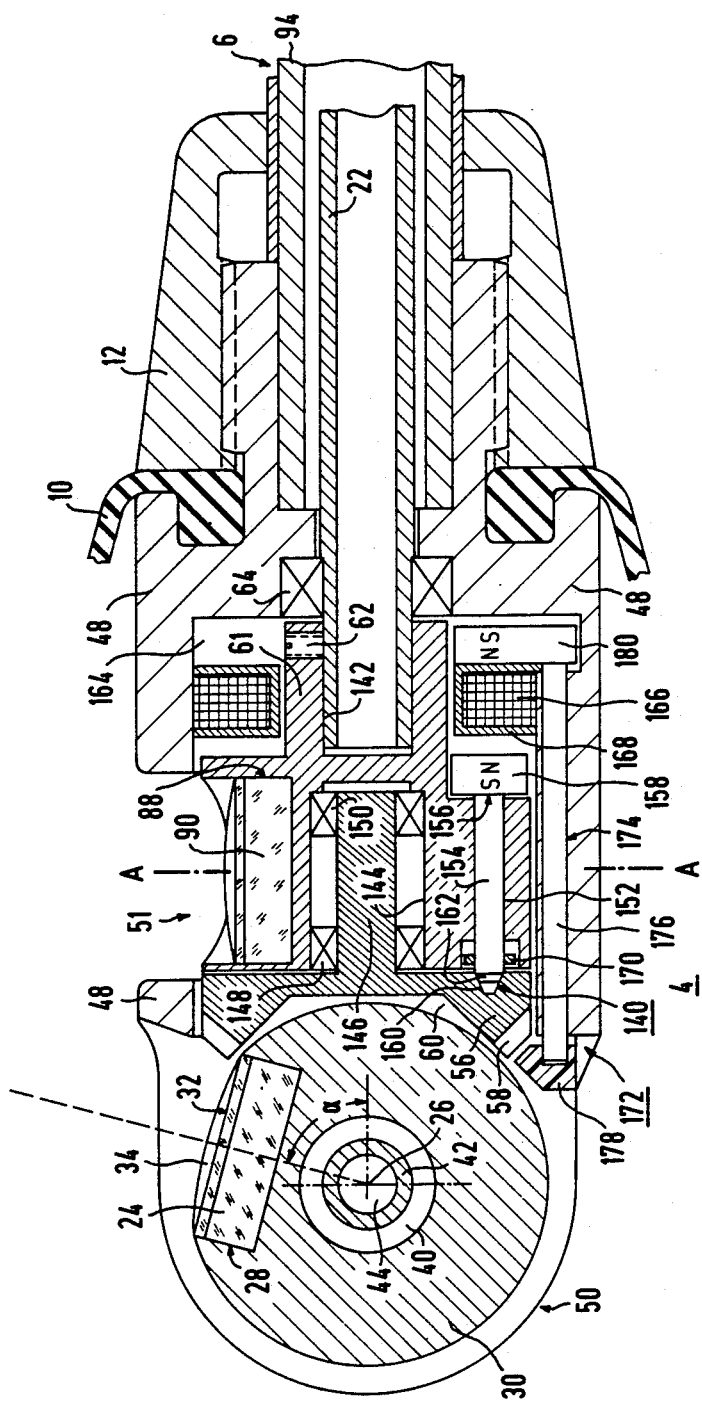
FIG. 3 is a sectional view perpendicular to the sectional view of FIG. 2 through an ultrasound scanner means which is provided for Doppler flow measurement and wherein an ultrasound transducer is coupled to the drive shaft via a coupling.

The exemplary embodiment of FIG. 3 allows both an ultrasound scanning of two examination surfaces as well as the scanning in only one examination surface given simultaneous flow measurement based on the Doppler principle. The examination head 4 is constructed similar to the one shown in FIG. 2. The same reference characters are used for identical parts. Here, the second ultrasound transducer 90 is likewise rigidly coupled to the drive shaft 22 via the holding part 61. The first ultrasound transducer 24, however, is coupled to the drive shaft 22 via a releasable coupling 140.

For purposes of a better overview, the cladding 10 of the examination head 4 is only partially shown in FIG. 3. However, it here also surrounds the entire, front part of the examination head 4.

Unlike FIG. 2, the holding part 61 here does not have its entire length plugged over the drive shaft 22, but comprises a blind hole 142 in which the drive shaft 22 is mounted. A further blind hole or a central bore 144 is introduced into the holding part 61 at that side lying opposite the blind hole 142. The second bevel gear 56 herein is provided with a central tappet 146 which projects into the blind hole 144 and is seated there. Bearing is provided with two further ballbearings 148, 150.

The outside diameter of the holding part 61 increases in the region of the further blind hole 144. As a result thereof, space is created in the holding part 61 so that the second ultrasound transducer 90 is completely introduced into the substance 88. The scanned direction of the ultrasound transducer 90 here—differs from that described in FIG. 2—is aligned perpendicular to the drive shaft 22. The bevel gear 56 is detachably connected to the holding part 61 via the coupling 140 set forth below. A bore 152 is opposite the substance 88. This bore 152 is laterally offset relative to the blind holes 142 and 144 and is aligned parallel to the latter.

A pin 154 is mounted in the bore 152. The pin 154 is displaceable in the bore 152. A block-shaped, first permanent magnet 158 is secured at that end 156 of the pin 154 which faces away from the bevel gear 56. The north pole of the permanent magnet 158 is N and the south pole is S.

A conical recess 160 is introduced in the bevel gear 56 lying opposite the pin 154. In FIG. 3, the pin 154 has its end 162 engaging into the recess 160. The second gear 56 is mechanically connected to the drive shaft 22 via this pin 154 and via the holding part 61.

A clearance 164 is created inside the housing 48 in the region of the blind hole 142. An electromagnetic annular coil 166 which is wound onto a coil body 168 is located in this clearance 164 concentrically relative to the drive shaft 22. The annular coil 166 is secured in the housing 48 via the coil body 168. The inside diameter of the coil body 168 is somewhat larger than the outside diameter of the holding part 61, so that the holding part 61 can freely turn.

With respect to the permanent magnet 158, the annular coil 166 is arranged such that a good magnetic interaction with the permanent magnet 158 is present at every position of the rotatable holding part 61 given a current-permeated annular coil 166, i.e. the permanent magnet 158 and annular coil 166 are arranged with a slight spatial distance from one another.

When the annular coil 166 is excited by a first direction of current flux, a magnetic field distribution which repels the permanent magnet 158 away from the annular coil 166 derives; i.e., given the polarization of the permanent magnet 158 indicated in FIG. 3, a magnetic north pole is generated by the annular coil 166 at that side lying opposite the permanent magnet 158. The coupling thereby mechanically connects the second gear 56 to the drive shaft 22 via the pin 154 and the holding part 61. In this position of the pin 154, thus, the first ultrasound transducer 24 is coupled to the drive shaft 22 and rotates around the axis 26 during rotation of the drive shaft 22. Simultaneously, the ultrasound transducer 90 rotates around the longitudinal axis of the drive shaft 22. Two examination planes which lie perpendicularly relative to one another and partially intersect can now be displayed on the picture screen, as set forth in the case of the exemplary embodiment of FIG. 2.

When the direction of the current in the annular coil 166 is reversed, i.e. the annular coil 166 is charged with a current in the second direction of current flux, and the magnetic field generated by the annular coil 166 also changes. A magnetic south pole generated by the annular coil 166 now lies opposite the permanent magnet 158. The pin 154 is withdrawn from the recess 160 in the direction toward the annular coil 166. A detent 170 which is rigidly connected to the pin 154 allows a movement of the pin 154 in the direction toward the magnetic coil 166 only to such an extent until it strikes the floor of an expanded part of the bore 152. This prevents the permanent magnet 158 from touching the coil body 168.

A brake 172 prevents a rotation of the first ultrasound transducer 24 when it is uncoupled from the drive shaft 22. To this end, a bore 174 is introduced in the housing 48 parallel to the drive shaft 22. The bore extends in the housing from the ultrasound window 50 up to the clearance 164, i.e. and the length of the bore 174 roughly corresponds to the distance between the bevel gear 56 and the annular coil 166. This brake pin 176 projects from the bore 174 at the ultrasound window 50. A brake block 178 is attached at this end of the pin 176. A second permanent magnet 180 is secured to the other end of the brake pin 176, this second permanent magnet 180 being arranged at that side of the annular coil 166 lying opposite the first permanent magnet 158. The polarization of the permanent magnet 180 is such that those sides of the two permanent magnets 158 and 180 lying closest to one another have identical poles. In FIG. 3, the north pole of the permanent magnet 180, referenced N, is indicated at the left, whereas the south pole, referenced S, is indicated at the right.

When the annular coil 166 is charged with a current in the first direction of current flux, then, as already set forth, the permanent magnet 158 is repelled away from the annular coil 166. Simultaneously, the permanent magnet 180 is attracted by the annular coil 166. In this condition, the permanent magnet 180 touches the coil body 168. A distance between the brake block 178 and the toothing 58 of the gear 56 thereby occurs, i.e. the brake 172 is not in engagement and the gear 56 is freely rotatable via the drive shaft 22. When the direction of current flux in the coil 166 is reversed, then the permanent magnet 158, as already set forth, is attracted by the coil 166 whereas the permanent magnet 180 is repelled away from the coil 166, i.e. the coupling 140 is released and the brake 172 has its brake block 178 acting on the teeth 58 of the bevel gear 56. The position in which the ultrasound transducer 24 is located at that moment is thus fixed. The drive shaft 22 can now only drive the ultrasound transducer 90. The bevel gear 56 stands still, whereas the holding part 61 turns around the tappet 146 of the bevel gear 56.

Figure 4:
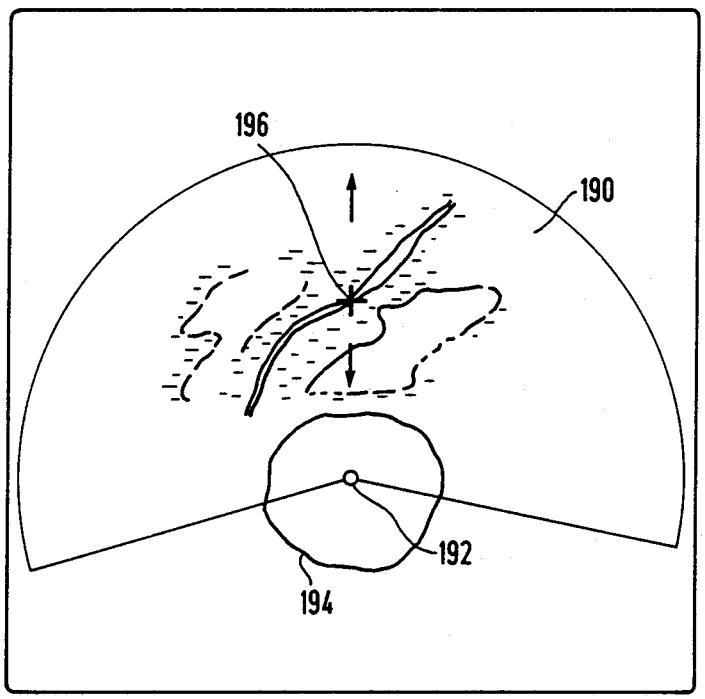
FIG. 4 illustrates a monitor image of the examination surface which is generated by the ultrasound scanner means of FIG. 3 and which is referenced A—A in FIG. 3.

FIG. 4 is an illustration, for example, of the display on the monitor of the ultrasound scan means and shows the examination surface scanned by the ultrasound transducer 90. This is a surface in the shape of a circular sector 190 in the plane referenced A—A in FIG. 3. The sector origin 192 is the longitudinal axis of the drive shaft 22. An approximately circular line 194 which is located around the sector origin 192 represents the wall of the body cavity in which the examination head 4 is located. In order to initiate the Doppler flow measurement, the entire examination head 4 of the ultrasound scanner means 2 is rotated in the body cavity until the specimen to be examined or the "region of interest" (ROI) is located in the middle of the sector image 190. A mark 196 displaceable on the monitor picture A—A is now shifted onto the location of the specimen to be examined (ROI). The position of the mark 196 on the monitor picture determines the angle alpha which the ultrasound transducer 24 must assume relative to the longitudinal axis of the drive shaft 22. This angle is calculated in the ultrasound scanner means 2 from the position of the mark 196. The ultrasound transducer 24 is now set to this calculated angle alpha at low-speed. When the rated value coincides with the actual value of the angle alpha, the coupling 140 is released and, simultaneously, the brake 172 is thereby actuated. The ultrasound transducer 24 is then switched to Doppler flow measurement in the ultrasound scanner means 2, i.e. it measures of the velocity fluid in the vessel via the frequency shift of the emitted ultrasound pulse. During the Doppler flow measurement, the ultrasound transducer 90 can simultaneously execute a B-sector scan in the plane A—A, ie. the location of the Doppler flow measurement can be precisely observed in the sector image A—A on the monitor. A positional modification of the examination head 4 or of the specimen in the body is immediately recognized.

Figure 5:
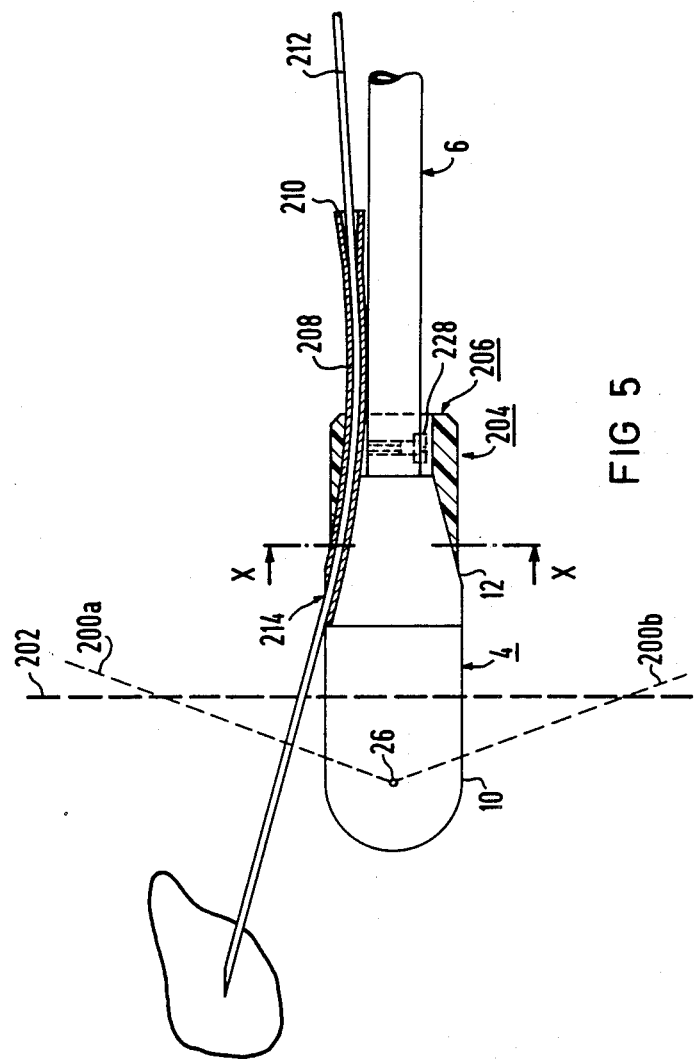
FIG. 5 is a plan view, shown partially in section, of an examination head of an ultrasound scanner means comprising a biopsy needle guide.

In FIG. 5, 4 is the examination head of an ultrasound scan means 2. The two broken lines 200a, 200b which have their origin in the axis 26 indicate the boundary of the section or examination plan which is scanned by the ultrasound transducer 24. This examination plane lies in the plane of the paper. The second section or examination plane which is scanned by the ultrasound transducer 90 which—as in FIG. 3—scans perpendicular to the drive shaft 22 is indicated by the broken line 202. This examination plane lies perpendicular to the plane of the paper. The examination head 4 is connected to the housing head 8 (not shown here) via the guide 6. The nut 12, as set forth in FIG. 1, also holds the cladding 10 firmly on the examination head 4.

A biopsy needle guide 204 is arranged at the transition from the guide 6 to the tightening nut 12. The biopsy needle guide 204 is composed of a clamp mechanism 206 and of a bent guide tube 208. The guide 208 is arranged in the direction of the drive shaft 22 (not shown here), i.e. in the longitudinal direction of the guide 6. It contacts both the guide 6 as well as the tightening nut 12. At its proximal end or at its admission opening 210, the guide tube 208 is widened to be funnel-shaped so that a biopsy needle 212 can be easily introduced. Further, the proximal opening 210 is aligned at a slant relative to the longitudinal axis of the drive shaft 22, i.e. the biopsy needle 212 moves away from the guide 6 with increasing distance from the clamp mechanism 206. As a result of this slanted positioning of the proximal opening 210, the biopsy needle 210 is conducted past the housing head 8 (not shown here). The manipulation of the biopsy needle 212 is thereby facilitated.

The distal end or the discharge opening 214 of the guide tube 208 is likewise arranged at a slant relative to the drive shaft 22 or, respectively, relative to the guide 6. A biopsy needle 212 can be guided in the guide tube 208 and has a slanted alignment relative to the guide 6 at its distal end as well. As a result thereof, regions in the body of a patient which lie behind the wall of the body cavity can also be reached in a simple way. For example, it is possible to perform a biopsy on the prostate via the intestines in this way.

The biopsy needle guide 204 is secured such to the examination head 4 that the biopsy needle lies in the examination plane during the examination, this examination plane being that plane scanned by the first ultrasound transducer 24. At the same time, the biopsy needle 212 can also be observed in the second examination plane scanned by the ultrasound transducer 90. The path of the biopsy needle 212 in the body can be precisely observed via the two ultrasound examination planes. This thus creates possibilities of also carrying out examinations under difficult circumstances. The examination risk is thereby kept low.

Figure 6:
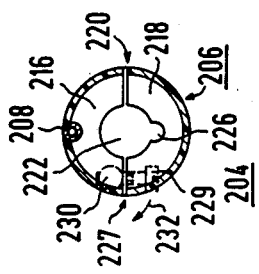
FIG. 6 is a front view of the biopsy needle guide of FIG. 5.

FIG. 6 shows the biopsy needle guide 204 in a view referenced X—X in FIG. 5. The clamp mechanism 206 is essentially cylindrical at the outside. It is composed of two holding parts 216, 218 that are connected to one another via a hinge 220. The guide tube 208 is thereby secured in the holding part 216. In its closed condition, the clamp mechanism 206 comprises a central opening 222. The contour of the central opening 222 is at least partially matched to the outside contour of the examination head at the point of transition to the guide 6. Here, the opening 222 has a cylindrical and a conical part. The two holding parts 216, 212, have the shape of a half cylinder, these parts forming a cylinder when clamped with a closed clamping mechanism 206, with an important difference that they do not touch when held by the closed clamp mechanism 206.

Both holding parts 216, 218 are preferably composed of an elastic plastic, for example, of polypropylene.

The hinge 220 that connects the two holding parts 216, 218 to one another is what is referred to as a film hinge 220 here. Both holding parts 216, 218 and the film hinge 220 are thereby advantageously manufactured in common with an injection molding process.

A groove 226 is introduced into the cylindrical part of the opening 222. This groove accepts a rib 222 which is located on the guide 6 and is shown in FIG. 5. As a result thereof, the relative position of the biopsy needle guide 204 relative to the examination head 4 is fixed.

A closure 227 for the clamp mechanism 206 is arranged at that side lying opposite the hinge 220. The closure 227 is composed of a screw 229 that can be screwed into a pin or bolt 230. This pin or bolt 230 is rotatably seated in the holding part 216. A slot formed into the holding part 218 allows the screw to be swiveled in the direction of the arrow 232. The clamp mechanism can then be folded apart.

The overall biopsy needle guide 204 is composed of a material sterilizable with hot steam. Before application for biopsy, a sterilized, thin coating is pulled over the examination head 4. After this, the sterilized biopsy needle guide 204 is held at the examination head 4 in its folded open condition such that the rib 228 lies in the groove 226. The groove 226 and the rib 228 form a guide which fixes the relative position of the biopsy needle guide 204 relative to the examination head 4. The clamp mechanism 206 is closed with the closure 227, i.e. the two holding parts 216, 218 are held fast via the screw 227. The biopsy needle 204 is thus secured to the examination head 4 in a defined position.

In that the outside dimensions of the biopsy needle guide 204 do not project beyond the outside dimensions of the examination head 4, the introduction of the examination head 4 into a body cavity is not impeded. The examination head 4 is aligned such in the body cavity that the region of interest (ROI) lies in the examination plane scanned by the ultrasound transducer 24. The fixed, defined position of the guide tube 208 with reference to the examination head 4 guarantees that the biopsy needle 212 can be introduced only in this plane. Given the simultaneously possible observation of the feed path in the further examination plane scanned by the ultrasound head 90, impediments potentially present that are not visible in the first examination plane can be recognized.

Although the invention has been described with respect to preferred embodiments, it is not to be so limited as changes and modifications can be made which are within the full intended scope of the invention as defined by the appended claims.

I claim as my invention:

1. An intracavitary ultrasound scanning means adopted to be used in the human body comprising, an examination head, a first ultrasound transducer mounted in said head, said transducer being rotatable around an axis and positioned for scanning a first scan surface and driven by a drive shaft which has proximal and distal ends, said axis (26) is aligned substantially perpendicular to the distal end of said drive shaft (22); a first gear (52) connected to turn said first ultrasound transducer (24) around said axis (26), said first gear in engagement with a second gear (56) attached to the distal end of said drive shaft (22); a holding part (61) mounted on said drive shaft (22) for rotation therewith and, a second ultrasound transducer (90) attached to said holding apart and positioned for scanning a second scan surface with respect to said first plane.

2. An ultrasound scanning means according to claim 1, wherein the emission direction of said second ultrasound transducer (90) is aligned at a slant angle relative to the axis of said drive shaft (22).

3. An ultrasound scanning means according to claim 1, wherein said drive shaft (22) runs in a ballbearing (64) which is held by said housing (48).

4. An ultrasound scanning means according to claim 1, wherein said examination head is secured to a housing head via a guide, said drive shaft (22) is secured in said housing head (8) and to the output shaft (104) of an electric motor (106).

5. An ultrasound scanning means according to claim 4, characterized in that said drive shaft (22) is formed as a hollow shaft which has a greater wall thickness and-/or a greater diameter at its proximal end (22a, 22b) than at its distal end.

6. An ultrasound scan means according to claim 1, wherein said first ultrasound transducer (24) is attached to a drum (30) which is rotatable around a bearing axis (42) which is aligned along said axis (26); said drum (30) carries said first gear (52) at its face side, the teeth (54) of said first gear are in engagement with the teeth (58) of said second gear (56); and said second gear (56) is centrally fastened to the distal end of said drive shaft (22).

7. An intracavitary ultrasound scanning means comprising, an examination head, a first ultrasound transducer mounted in said head, said transducer being rotatable around an axis and driven by a drive shaft which has proximal and distal ends, said axis (26) is aligned substantially perpendicular to the distal end of said drive shaft (22); a first gear (52) connected to turn said first ultrasound transducer (24) around said axis (26), said first gear in engagement with a second gear (56) attached to the distal end of said drive shaft (22) and, a second ultrasound transducer (90) attached to said holding part, and wherein said first and second gears are formed of first and second bevel gears (52, 56); and said second bevel gear (56) has a distally located depression (60) into which said first ultrasound transducer (24) passes as it is turned around said axis (26).

8. An ultrasound scan means according to claim 7, wherein said first ultrasound transducer (24) is attached to a drum (30) which is rotatable around a bearing axis (42) which is aligned along said axis (26); said drum (30) carries said first gear (52) at its face side, the teeth (54) of said first gear are in engagement with the teeth (58) of said second gear (56); and said second gear (56) is centrally fastened to the distal end of said drive shaft (22).

9. An ultrasound scanning means according to claim 8, wherein said bearing shaft (42) is as a hollow shaft.

10. An ultrasound scanning means according to claim 9, wherein said drum (30) has its other face side attached to the rotatable part (72, 76) of a variable transformer (70); and the non-rotatable part (78, 84) of said variable transformer (70) is connected to said bearing shaft (42).

11. An ultrasound scanning means according to claim 10, wherein said bearing shaft (42) is secured to a housing (48) which surrounds both said first and second gears (52, 56) which is provided with an ultrasound window (50) to allow passage of ultrasound pulses emitted by said first ultrasound transducer (24) and to receive echoes detected by said ultrasound transducer.

12. An ultrasound scanning means according to claim 11, wherein said housing (48) is surrounded by an elastic cladding (10).

13. An ultrasound scanning means according to claim 8, wherein said drum (30) is rotatably mounted on said bearing shaft (42) by means of at least one ballbearing (38, 40).

14. An intracavitary ultrasound scanning means comprising, an examination head, a first ultrasound transducer mounted in said head, said transducer being rotatable around an axis and driven by a drive shaft which has proximal and distal ends, said axis (26) is aligned substantially perpendicular to the distal end of said drive shaft (22); a first gear (52) connected to turn said first ultrasound transducer (24) around said axis (26), said first gear in engagement with a second gear (56)

attached to the distal end of said drive shaft (22); a holding part (61) is connected to said drive shaft (22) and, a second ultrasound transducer (90) attached to said holding part, and wherein said drive shaft (22) is a hollow shaft.

15. An intracavitary ultrasound scanning means comprising, an examination head, a first ultrasound transducer mounted in said head, said transducer being rotatable around an axis and driven by a drive shaft which has proximal and distal ends, said axis (26) is aligned substantially perpendicular to the distal end of said drive shaft (22); a first gear (52) connected to turn said first ultrasound transducer (24) around said axis (26), said first gear in engagement with a second gear (56) attached to the distal end of said drive shaft (22); a holding part (61) is connected to said drive shaft (22) and, a second ultrasound transducer (90) attached to said holding part, wherein said examination head is secured to a housing head via a guide, said drive shaft (22) is secured in said housing head (8) and to the output shaft (104) of an electric motor (106), and wherein the rotatable part (126, 128) of a variable transformer (124) is mounted at the proximal end of said output shaft (104).

16. An ultrasound scanning means according to claim 15, characterized in that said drive shaft (22) is formed as a hollow shaft which has a greater wall thickness and/or a greater diameter at its proximal end (22a, 22b) than at its distal end.

17. An ultrasound scanning means according to claim 16, wherein said rotatable part (126, 128) of said variable transformer (124) is secured to the proximal face side of said drive shaft (22).

18. An ultrasound scanning means according to claim 17, wherein drive shaft (22) is surrounded by a carrier tube (94) mounted between said examination head (4) and said housing head (8), and said carrier tube being provided with a plastic cladding (14).

19. An intracavitary ultrasound scanning means comprising, an examination head, a first ultrasound transducer mounted in said head, said transducer being rotatable around an axis and driven by a drive shaft which has proximal and distal ends, said axis (26) is aligned substantially perpendicular to the distal end of said drive shaft (22); a first gear (52) connected to turn said first ultrasound transducer (24) around said axis (26), said first gear in engagement with a second gear (56) attached to the distal end of said drive shaft (22); a holding part (61) is connected to said drive shaft (22) and, a second ultrasound transducer (90) attached to said holding part, wherein said examination head is secured to a housing head via a guide, said drive shaft (22) is secured in said housing head (8) and to the output shaft (104) of an electric motor (106), and wherein a manual pump (16) is mounted in said housing head (8), said manual pump connected to pump up a cladding (10) surrounding said examination head (4) with ultrasound coupling fluid (66).

20. An ultrasound scanning means according to claim 19, wherein said manual pump (16) and said examination head (4) are connected together by a hydraulic line (133).

21. An ultrasound scan means according to claim 20, wherein said hydraulic line (133) discharges into a cavity (92) in said guide (6).

22. An intracavitary ultrasound scanning means comprising, an examination head, a first ultrasound transducer mounted in said head, said transducer being rotatable around an axis and driven by a drive shaft which has proximal and distal ends, said axis (26) is aligned substantially perpendicular to the distal end of said drive shaft (22); a first gear (52) connected to turn said first ultrasound transducer (24) around said axis (26), said first gear in engagement with a second gear (56) attached to the distal end of said drive shaft (22); a holding part (61) is connected to said drive shaft (22) and, a second ultrasound transducer (90) attached to said holding part, and wherein said first ultrasound transducer (19) is rigidly coupled to said drive shaft (22); and said second ultrasound transducer (24) is coupled to said drive shaft (22) via a releasable coupling (140).

23. An ultrasound scanning means according to claim 22, wherein a brake (172) is connected which prevents rotation of said second ultrasound transducer (24) when it is uncoupled from said drive shaft (22).

24. An ultrasound scanning means according to claim 23, wherein said coupling (140) mechanically connects said second gear (56) to said drive shaft (22).

25. An ultrasound scanning means according to claim 24, wherein said coupling (140) includes a pin (154) which is displaceable in a bore (152) in said holding part (61), said bore being parallel to said drive shaft (22); and in that a recess (160) is formed in said second gear (56), the one end (162) of said pin (154) engaging into said recess when said second ultrasound transducer (24) is coupled to said drive shaft (22).

26. An ultrasound scanning means according to claim 25, wherein a first permanent magnet (158) is attached to the other end (156) of said pin (154); and an annular coil (166) is concentrically arranged around said drive shaft (22), said annular coil being capable of entering into magnetic interaction with said first permanent magnet (158) such that, in a first direction of current flux, said pin (154) is pressed into said recess (160) and in a second direction of current flux, said pin (154) is pulled out of said recess (160).

27. An ultrasound scanning means according to claim 26, wherein said brake (172) includes a brake pin (176) which is displaceable in a bore (174) in said housing (48), said bore being parallel to said drive shaft (22); a brake block (178) secured to one end of said brake pin (176); a second permanent magnet (180) secured to the other end of said brake pin (174), said second permanent magnet arranged at the side of said annular coil (166) which lies opposite said first permanent magnet (158), whereby said annular coil (166) can enter into magnetic interaction with said second permanent magnet such that, in said first direction of current flux, said brake block (178) does not touch said second gear wheel (56) and such that, in said second direction of current flux, said brake block (178) presses against said second gear wheel (56).

28. An ultrasound scanning means according to claim 27, wherein said second gear (56) has a central tappet (146) which is seated in a central bore (144) in said holding part (61).

29. An ultrasound scanning means according to claim 20, wherein said second ultrasound transducer (24) is provided for generating a B-image when it is coupled to said drive shaft (22) and is provided to make Doppler flow measurements when it is uncoupled from said drive shaft (22).

30. An ultrasound scanning means according to claim 29, wherein the location of said Doppler flow measurement can be portrayed in said B-image.

31. An intracavitary ultrasound scanning means comprising, an examination head, a first ultrasound transducer mounted in said head, said transducer being rotatable around an axis and driven by a drive shaft which has proximal and distal ends, said axis (26) is aligned substantially perpendicular to the distal end of said drive shaft (22); a first gear (52) connected to turn said first ultrasound transducer (24) around said axis (26), said first gear in engagement with a second gear (56) attached to the distal end of said drive shaft (22); a holding part (61) is connected to said drive shaft (22) and, a second ultrasound transducer (90) attached to said holding part, and wherein a biopsy needle guide (204) which includes a tube guide (208) and a clamp mechanism (206) is detachable connected to said examination head (4); said guide tube (208) is laterally offset and arranged in the direction of said drive shaft (22); and the discharge opening (214) of the guide tube (208) is aligned at a slanting direction relative to said drive shaft (22).

32. An ultrasound scanning means according to claim 31, wherein said clamp mechanism (206) includes two holding parts (216, 218) which, in their closed condition form a central opening (222) with a contour which is at least partially matched to the outside contour of said examination head (4) and said two holding parts (216, 218) are connected to one another by a hinge (220).

33. An ultrasound scanning means according to claim 31 or 32, wherein the admission opening (210) of said guide tube (218) is likewise aligned at a slant angle relative to said drive shaft (22).

34. An ultrasound scanning means according to claim 31 or 32, wherein said admission opening (210) of said guide tube (208) is formed to be funnel-shaped.

35. An ultrasound scanning means according to claim 31 or 32, wherein a guide (226, 228) is provided which defines the relative position of said biopsy needle guide (204) relative to said examination head (4) such that a biopsy needle (212) guided in said guide tube (208) lies in one of the section planes of said examination head (4).

36. An ultrasound scanning means according to claim 31 or 32 wherein the outside dimensions of said biopsy needle guide (204) do not project beyond the outside dimensions of said examination head (4).

* * * * *